US00PP09873P

United States Patent [19]

Zaiger et al.

[11] Patent Number: Plant 9,873

[45] Date of Patent: Apr. 29, 1997

[54] PEACH TREE 'SNOW PRINCE'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 605,259

[22] Filed: Dec. 1, 1995

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach *Prunus persica* tree which has the following unique combination of features that are desirable in a new variety:

1. Heavy and regular bearer of large size fruit.
2. Producing mild, sub-acid fruit with very good flavor and eating quality.
3. Fruit with firm white flesh, good handling and shipping quality.
4. Fruit with a high degree of attractive red skin color.
5. Relatively uniform ripening of the fruit.
6. Vigorous, upright growth of the tree.

1 Drawing Sheet

ORIGIN OF THE VARIETY

The present new variety of peach tree was developed by us in our experimental orchard located near Modesto, Calif., as a second generation cross between two selected seedlings, field identification numbers 24GA795 and 24R215. The maternal parent, field identification number 24GA795 , originated from a cross between Red Grand Nectarine (U.S. Plant Pat. No. 1,060) and Redwing Peach (U.S. Plant Pat. No. 621). The paternal parent, field identification number 24R215, originated as a seedling selection developed from the cross of O'Henry Peach (U.S. Plant Pat. No. 2,964) and Giant Babcock Peach (U.S. Plant Pat. No. 1,353), crossed with Top Crest Peach (U.S. Plant Pat. No. 5,745). We grew and maintained a large group of these second generation seedlings under careful observation, during which time we recognized its desirable fruit characteristics and selected the present variety for asexual reproduction and commercialization.

ASEXUAL REPRODUCTION OF THE VARIETY

The new and distinct variety of peach tree was asexually propagated by budding, as performed by us in our experimental orchard located near Modesto, Calif., and shows that such reproductions run true to the original tree and all said characteristics are established and transmitted through succeeding asexual propagations.

SUMMARY OF THE VARIETY

The present new and distinct variety of peach tree is of large size; vigorous, upright growth; and a productive and regular bearer of large, firm, white flesh, clingstone fruit with very good flavor and eating quality. The fruit is further characterized by being relatively uniform in ripening throughout the tree; having a high degree of attractive red skin color; having good handling and storage quality; ripening in the early maturing season; and in comparison to the early maturing, yellow flesh Top Crest Peach (U.S. Plant Pat. No. 5,745) fruit, the new variety has white flesh, greater production of larger size fruit, more attractive red skin color and is approximately 26 days later in maturity.

BRIEF DESCRIPTION OF THE PHOTOGRAPH

The accompanying photographic illustration shows typical specimen of the fruit and foliage of our new peach variety. Illustrated are the upper and lower surface of the leaves, a specimen showing the exterior and sectional view of a fruit divided in its suture plane to reveal flesh coloration, pit cavity and a stone remaining in place. The photograph was taken shortly after being picked at maturity (firm ripe), and the colors are as nearly true as is reasonably possible in a color representation of this type.

DESCRIPTION OF THE VARIETY

The following is a detailed botanical description of the present new variety of peach tree, its flowers, foliage and fruit as based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Medium stocky.
- *Surface.*—Medium shaggy.
- *Color.*—Hair brown to brown (5-E-4) to (5-E-6).

Branches:
- *Size.*—Medium.
- *Surface.*—Smooth to medium rough, varies with age of growth.
- *Lenticles.*—Medium number. Medium Size.
- *Color.*—Yellowish brown to brown (5-D-7) to (5-E-6).

Leaves:
- *Size.*—Large. Average length 6½". Average width 1½".
- *Form.*—Lanceolate, pointed.
- *Surface.*—Smooth.
- *Margin.*—Crenate.
- *Thickness.*—Medium.
- *Petiole.*—Medium length. Medium thickness.
- *Glands.*—Reniform. Number varies from 1 to 5. Average number 3. Positioned on upper portion of petiole and base of leaf blade.
- *Color.*—Upper surface —green to dark green (28-F-7) to (28-F-8). Lower surface —dull green to green (28-E-5) to (28-E-7).

Flower buds:
*Size.*—Medium to large.
*Length.*—Medium.
*Form.*—Plump.
Flowers:
*Size.*—Large, showy.
*Blooming period.*—Mar. 6, 1993 to Mar. 10, 1993. Varies slightly with climatic conditions.
*Color.*—Pink.
*Pollen.*—Present.
Fruit:
*Maturity when described.*—Firm ripe.
*Date of first picking.*—Jun. 6, 1993.
*Date of last picking.*—Jun. 9, 1993. Varies slightly with climatic conditions.
*Size.*—Large, comparatively uniform. Average diameter axially 3". Average transversely in suture plane 3".
*Form.*—Nearly globose, slightly flattened at stem end.
*Suture.*—Nearly rounded.
*Ventral surface.*—Usually round, varies from slight depression to slightly enlarged.
Cavity Rounded to slightly elongated in suture plane. Average depth ½". Average breadth 1".
*Base.*—Retuse.
*Apex.*—Varies from round to slight pistil point.
Flesh:
*Ripens.*—Evenly.
*Texture.*—Firm.
*Juice.*—Moderate.
*Fibers.*—Few, tender.
*Flavor.*—Very good, mild, sub-acid, sweet.
*Eating quality.*—Very good.
*Amyqdalin.*—Undetected.
*Aroma.*—Moderate.
*Color.*—White to milkish white (1-A-1) to (1-A-2), varies slightly with maturity of fruit. Pit cavity, white to grayish white (1-A-1) to (1-B-1).
Skin:
*Thickness.*—Medium.
*Texture.*—Medium.
*Tendency to crack.*—None.
*Down.*—Moderate, short.
*Color.*—White to pinkish white ground color (9-A-1) to (9-A-2). Nearly overspread with red to deep red (10-B-8) to (10-D-8).
Stone:
*Type.*—Clingstone.
*Size.*—Large. Average length 1½". Average breadth 1⅛". Average thickness ⅝".
*Form.*—Oval to ovoid.
*Surface.*—Irregularly furrowed toward apex, pitted toward base. Pits vary from round to elongated.
*Sides.*—Equal to unequal.
*Ridges.*—Usually rounded.
*Apex.*—Varies from rounded to acute.
*Base.*—Usually rounded, varies from rounded to straight.
*Tendency to split.*—Very slight.
*Color.*—Light brown to brown (6-D-5) to (6-E-5).
Use: Dessert.
*Market.*—Local and long distance.
Keeping quality: Good.
Shipping quality: Good.

The present variety of peach tree, its flowers, foliage and fruit herein described may vary in slight detail due to climate, soil conditions, and cultural practices under which the variety may be grown, the present botanical description is that of the variety grown under the ecological conditions prevailing near Modesto, Calif.

We claim:

1. A new and distinct variety of peach tree, substantially as illustrated and described, characterized by its large size, vigorous and upright growth, and a productive and regular bearer of large, white flesh, clingstone fruit with very good flavor and eating quality; the fruit is further characterized by having firm flesh with good handling and shipping quality, having a high degree of attractive red skin color, and in comparison to the early maturing, Top Crest Peach (U.S. Plant Pat. No. 5,745) the new variety has white flesh instead of yellow flesh with heavier production of larger size fruit.

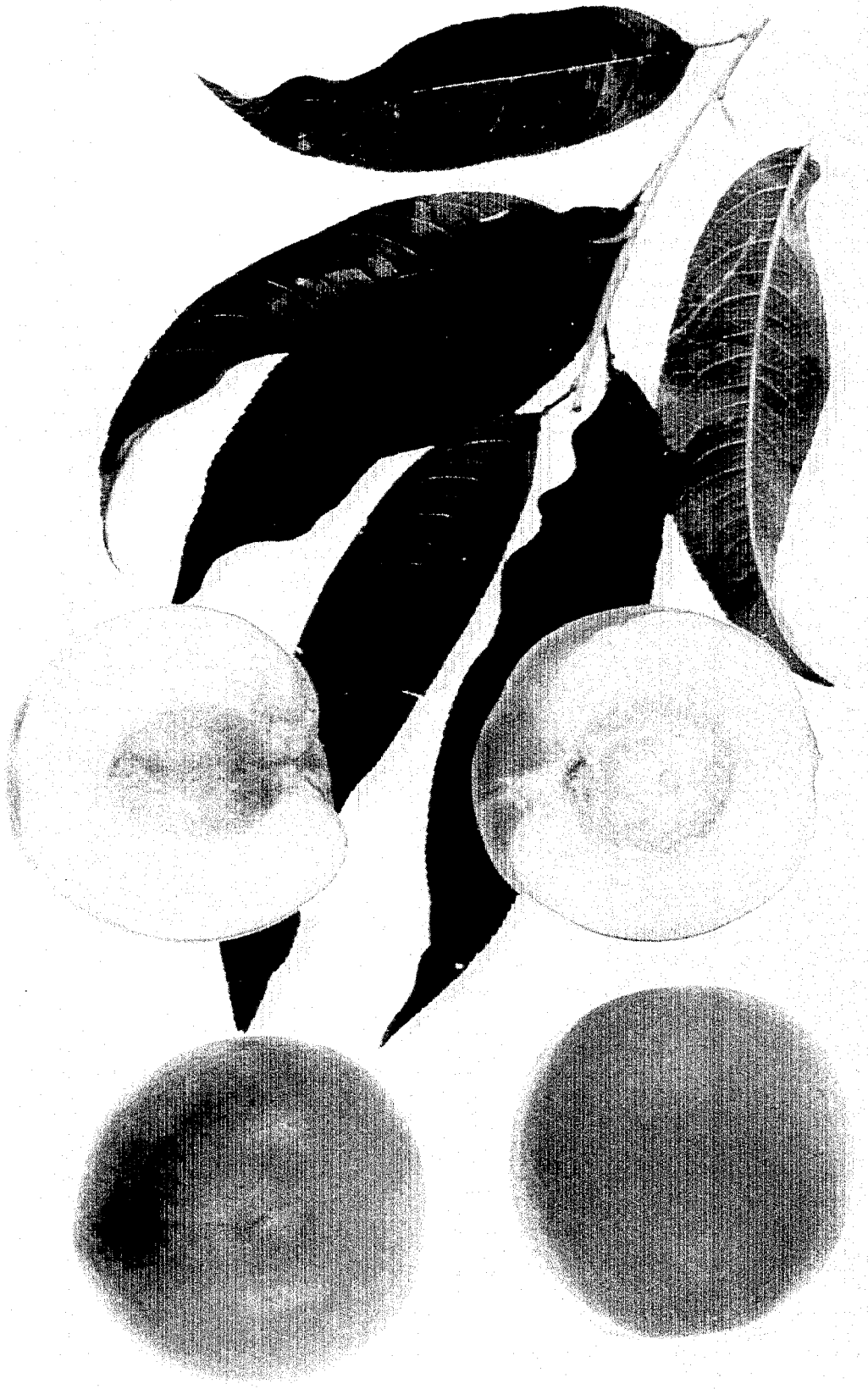

* * * * *